United States Patent [19]

Arrhenius

[11] 4,451,383

[45] May 29, 1984

[54] RECYCLABLE HOT PAD

[75] Inventor: Gustaf O. Arrhenius, La Jolla, Calif.

[73] Assignee: American Hospital Supply Corporation, Evanston, Ill.

[21] Appl. No.: 74,955

[22] Filed: Sep. 13, 1979

Related U.S. Application Data

[62] Division of Ser. No. 866,695, Jan. 3, 1978, Pat. No. 4,331,556.

[51] Int. Cl.$^3$ ............................. C09K 5/06; F24J 3/04
[52] U.S. Cl. ........................................ 252/70; 23/296; 23/300; 23/301; 23/302 R; 23/302 T; 126/263; 252/408.1; 252/962; 374/159; 423/266; 423/268; 423/514; 436/2
[58] Field of Search ..................... 252/70, 408.1, 962; 73/356, 358; 436/2; 126/263; 23/302 R, 300, 296, 302 T, 301; 423/266, 268, 514; 374/159

[56] References Cited

U.S. PATENT DOCUMENTS

| | | | |
|---|---|---|---|
| 1,894,775 | 1/1933 | Levenson | 252/70 |
| 2,044,942 | 6/1936 | Heckert | 23/300 |
| 2,118,586 | 5/1938 | Bowles et al. | 252/70 |
| 2,595,238 | 5/1952 | Frejacques | 23/300 |
| 2,677,243 | 5/1954 | Telkes | 252/70 |
| 2,706,716 | 4/1955 | Howe et al. | 23/300 |
| 3,271,106 | 9/1966 | Nylander | 252/70 |
| 3,539,291 | 11/1970 | Chiola et al. | 23/300 |
| 3,598,544 | 8/1971 | Teot | 23/300 |
| 3,859,856 | 1/1975 | Keele et al. | 73/358 |
| 3,913,559 | 10/1975 | Dandliker | 252/70 |
| 3,951,127 | 4/1976 | Watson et al. | 252/70 |
| 4,037,650 | 7/1977 | Randall | 252/70 |
| 4,263,050 | 9/1981 | Yamanaka et al. | 252/70 |
| 4,331,556 | 5/1982 | Arrhenius | 252/70 |
| 4,361,491 | 11/1982 | Truelock | 252/70 |

FOREIGN PATENT DOCUMENTS

2844810  5/1979  Fed. Rep. of Germany ........ 252/70

OTHER PUBLICATIONS

Svanoe, H., Chem. Eng. Progress, vol. 55, No. 5, pp. 47–54, (1959).

*Primary Examiner*—Teddy S. Gron
*Attorney, Agent, or Firm*—Ellsworth R. Roston; Charles H. Schwartz

[57] ABSTRACT

A liquid melt becomes converted to crystalline form at a particular temperature either spontaneously or when artificially nucleated. The liquid releases heat at crystallization. If the liquid is in a supercooled state when it begins to crystallize, its temperature will rise from the particular temperature at which it is nucleated.

Another liquid material is mixed with the liquid to be crystallized. The liquid additive has properties of forming a metastable solid together with the crystallizing material. When the liquid additive exsolves, the crystalline aggregate is weakened and is easily decomposed into fragments of small size. The liquid additive materials may include monohydric alcohols, diols and triols. The liquid additive material may be included in the liquid to be crystallized, in small amounts, amounts to two percent (2%) to five percent (5%) being typical. The amount and relative metastability of the liquid additive material in the solution contributes to control of the size of the crystals which are ultimately produced when the supercooled fluid crystallizes. A small amount of surface active material may also be included to modify the characteristics of the metastable solid solution, the exsolution process, and the texture of the exsolved crystal aggregate.

4 Claims, 5 Drawing Figures

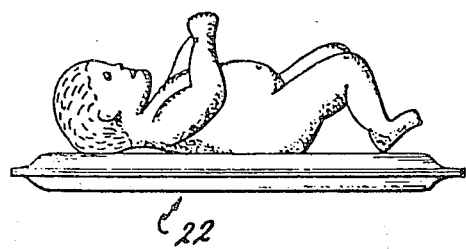
Fig. 1
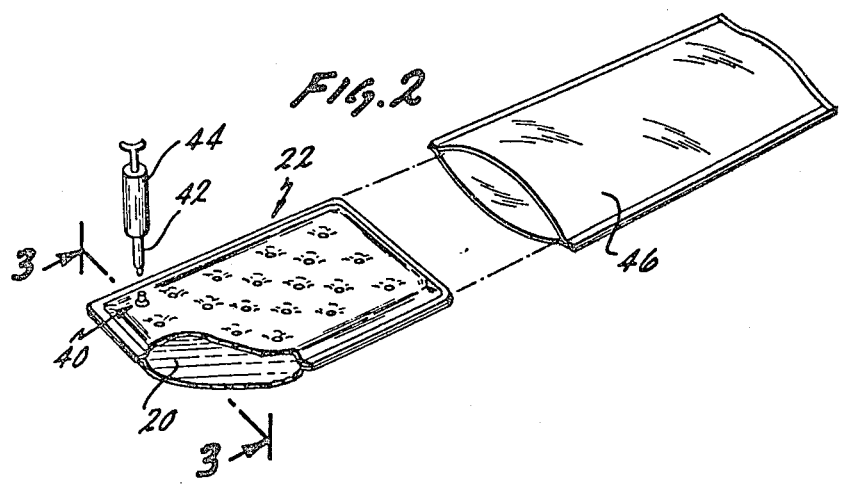
Fig. 2
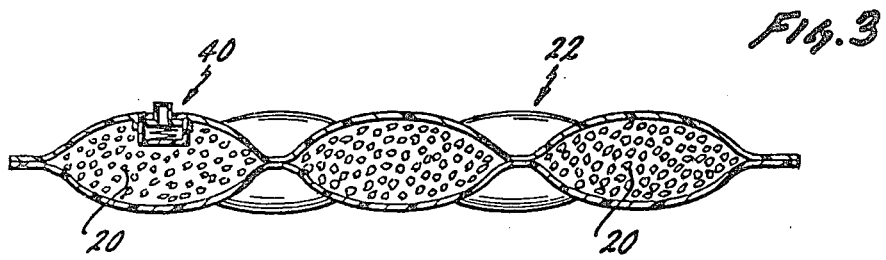
Fig. 3
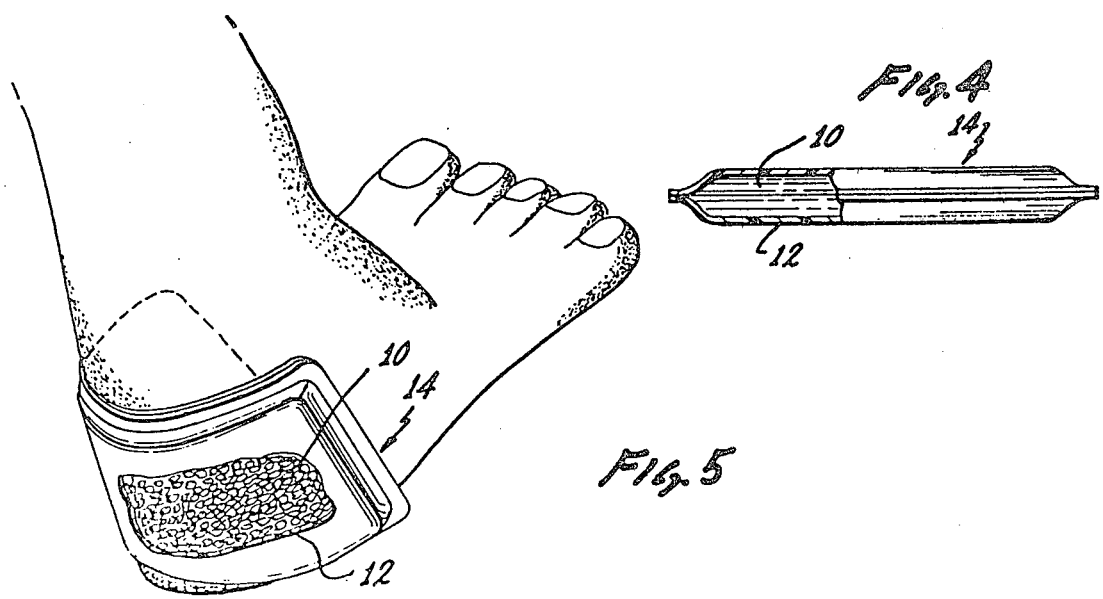
Fig. 4
Fig. 5

RECYCLABLE HOT PAD

This is a division, of application Ser. No. 866,695, filed Jan. 3, 1978 now U.S. Pat. No. 4,331,556.

This invention relates to recyclable hot pads or containers for generating heat at a controlled temperature for extended periods of time. More particularly, the invention relates to hot pads in which the material in the pads is provided in a form during the generation of heat such that the pads can be comfortably applied to the body of a patient for an efficient transfer of heat to the patient's body. The invention also relates to a method of forming such pads.

As medical science becomes advanced, it is increasingly important to apply heat at controlled temperatures to a patient for extended periods of time in order to optimize the beneficial effects of such heat on the patient. For example, it is often difficult to obtain blood from a baby for performing tests on the baby. It has been found that blood can be withdrawn most easily from the heel of a baby, particularly when the heel has been heated to a particular temperature. Since the baby cannot express in any easily identifiable way when the heat becomes excessive, babies sometimes become burned by the application of excessive heat.

As another example, it is often desirable to dispose a baby on a mattress which has been heated to a particular temperature. The mattress has to be comfortable to the baby at the same time that heat is being applied at the particular temperature to the baby. For example, the mattress should not be lumpy or provide sharp projections since the lumps or sharp projections affect the comfort of the baby.

Preferably the heat pads or containers should be recyclable. In other words, the pads should be capable of being used more than once to generate heat at the particular temperature. In this way, the cost of the pads can be amortized over a number of uses so that the cost per use is relatively low.

Heat pads have been provided in the prior art which meet a number of the objectives discussed above. For example, heat pads have been provided which are able to operate on a recyclable basis. Such heat pads have used supercooled melts which are nucleated at a particular temperature to become crystallized and to generate heat as the melts crystallize. Such heat pads employing supercooled liquid melts have been recyclable since the crystalline solid can be heated at the particular temperature to change the crystals to liquid state and the liquid state can then be retained in a metastable form at temperatures below the particular melting temperature. However, it has been difficult to provide for the material a melting temperature which provides optimal results. For example, when the material is to be used as a hot pack for babies to facilitate the withdrawal of blood from the babies, a melting temperature of approximately 104° F. for the crystalline solid is considered as optimal. Such a temperature has been difficult to obtain in a heat pack having the desired metastable characteristics. Furthermore, it has been difficult to inhibit the spontaneous crystallization of the supercooled melts at low temperatures such as temperatures below 32° F.

It has also been difficult to provide the crystals with a uniformly small size. It has further been difficult to provide the crystals with a size which is predetermined in accordance with the use to be made of the crystals. For example, crystals of one size may be desired for heel pads for babies and crystals of a different size may be desired for baby mattresses.

This invention provides heat pads or containers which overcome the above difficulties. The heat pads can be controlled to produce crystallization of a liquid in the heat pads at any pre-selected temperature between the melting point and the temperature of spontaneous nucleation. The crystallization can also be controlled such that crystals in any desired size range can be produced. In this way, the size of the crystallites can be adapted to the particular use that is to be made of the heat pads. As the melt crystallizes, it liberates heat so that the temperature rises from the particular temperature to a maximum temperature, which may coincide with, but does not exceed, the melting temperature. The heat pads are recyclable since they include liquids which become crystallized in the particular temperature range to generate heat and which become converted back to liquid form by the subsequent application of heat at or above the melting temperature. The melt in the heat packs has characteristics of remaining as a liquid in a metastable form at temperatures below the particular melting temperature until such time as the generation of heat is again desired.

Preferably the liquids in the heat pads of this invention are supercooled. Different liquid phases may be used depending upon the particular temperature interval in which the heat is to be generated.

The heat pads of this invention also include an additive liquid-phase material. The liquid additive material may be preferably selected from a group consisting of monohydric alcohols, diols and triols. The liquid additive material has properties of dissolving metastably in the crystals and to exsolve so as to limit the ultimate size of the crystallites. The amount and chemical properties of the liquid additive material in the supercooled melt contribute to control of the size of the crystallites that are produced when the supercooled fluid is nucleated to form one or several crystalline solids. Preferably, the amount of the liquid additive material in the supercooled melt for controlling the size and texture of the crystallites produced from the supercooled fluid should not exceed approximately two percent (2%) to five percent (5%) by weight.

It will be appreciated, however, that amounts of the liquid additive material in excess of two percent (2%) to five percent (5%) may be included in the liquid melt, particularly when it is desired to control the amount of heat generated by the melt. Under some circumstances, an amount of liquid-phase material in excess of two percent (2%) to five percent (5%) in the liquid melt may be advantageous in controlling the size and texture of the crystallites.

The liquid-additive material is also advantageous in controlling the particular maximum temperature which the supercooled melt reaches at crystallization. When the liquid additive material is used to provide such control of the melting temperature interval, it may exceed the preferable criterion of two percent (2%) by weight specified above, depending upon the particular temperature desired. The liquid additive material is also advantageous in inhibiting the uncontrolled and unintended spontaneous nucleation of the supercooled melt into incipient crystallization at low temperatures such as temperatures in the range of 0° F. to 35° F. Such control over such unintended nucleation into crystallization of the supercooled melt is especially important when the heat pads are shipped to distant destinations through winter climates with the melt in a supercooled state.

The effect of the liquid additive material in limiting the size of the crystals results from two different but related actions of the liquid additive material. In one action, the liquid additive material adsorbs to specific surfaces of the crystals so as to inhibit their growth. In another action, the adsorbed liquid additive material forms a metastable solid solution or dispersion in the crystals. This metastable solution or dispersion subsequently exsolves to form oriented vesicular liquid inclusions, which weaken the crystals and cause the crystals to break. The liquid inclusions also tend to cluster together and grow in size and thereby contribute to breaking up the crystals into fragments. These fragments can be given various sizes in the overall range of the order of ten (10) to one thousand (1,000) micrometers (μm) with consistency corresponding to that of sand or silt. If the heat pad is gently agitated as the crystals form, the achievement of this ultimate consistency is accelerated.

The heat pads may also include a small amount of a surface active material which is provided with properties of lowering the surface tension of the crystals produced from the melt such as the supercooled melt. The surface active material may be selected from a group consisting of sulfates, phosphates, phosphonates and sulfonates. The surface active material is preferably used when the liquid phase material constitutes particular ones of the liquid phase materials such as monohydric alcohols.

When the surface active material is used, the characteristics of the surface active material modify the rate of absorption and occlusion of the liquid additive. As a result, the texture of exsolved crystals aggregate, and the crystallites, can be modified beyond the limits imposed by the liquid additive. In those cases where the liquid additive has a limited solubility in the melt, such as in the case of certain monohydric alcohols as liquid additives, the use of appropriate surface active agents contributes to the stabilization of the liquid additive as a colloidal suspension in the melt.

The ability of the surface active material to affect the texture of the crystalline solid results from certain characteristics of such material. For example, the surface active material characteristically consists of longchain molecules with the terminal group on one end of the molecule having a high affinity for one or several of the components of the supercooled melt, and the other end having an affinity for the liquid additive. The distribution of the surface active material at the phase boundary between the supercooled melt and the liquid additive phase changes the surface energy of the system and causes the liquid additive to enter the supercooled melt, and the crystals forming from the melt, in a colloidal suspension. This colloidal suspension, when occluded in the crystalline phase, is in a metastable state, and tends to coalesce into larger exsolution vesicles, oriented on preferred crystallographic planes. The formation of these oriented exsolution vesicles weakens and disrupts the crystals so as to form small crystallites of size and shape dependent upon the combination of liquid additive material and surface active material on one hand and supercooled melt material on the other.

As will be seen from the above discussion, the use of a liquid additive material alone or the combination of a surface active material and a liquid additive material in a mixture with a heat-generating material such as a supercooled melt constitutes one feature of this invention. This combination provides a distinct advantage over such prior art as U.S. Pat. No. 3,770,390 issued to Teet on Nov. 6, 1973 and U.S. Pat. No. 3,653,847 issued to Abelson on Apr. 4, 1972, since neither of these patents discloses or contemplates the inclusion of additional material into a liquid such as a supercooled melt to limit the size of the crystals produced from such a melt.

In the drawings:

FIG. 1 is a side elevational view of a hot pad of the present invention when used as a baby mattress;

FIG. 2 shows in an exploded perspective relationship, partially broken away, the different members included in the baby mattress of FIG. 1;

FIG. 3 is a sectional view of the baby mattress of FIGS. 1 and 2 and illustrates the relative size of the crystals produced in such a mattress when the liquid melt in the mattress crystallizes to generate heat;

FIG. 4 is a side elevational view, partially broken away, of a heel pad applied to a baby to facilitate the withdrawal of blood from the baby; and FIG. 5 is a perspective view, partially broken away, of the heel pad of FIG. 4 when applied to the heel of a baby.

In one embodiment of the invention, a hot pack includes a liquid melt preferably having supercooled properties. A supercooled liquid melt has properties of crystallizing at a particular temperature to liberate heat. The crystallization occurs over an extended period of time, starting at the particular temperature and culminating at a temperature at or below the melting interval of the particular phase system so that the particular range of temperatures is produced for the extended period of time. When heat is subsequently applied to the resulting solid at or above its melting temperature interval, the solid returns to a liquid form and (unless nucleated) remains in the liquid form even at temperatures below the melting temperature interval. When the supercooled melt again becomes nucleated, it crystallizes again, while liberating heat. In this way, the melt is able to store heat until such time as it is desired to liberate the heat. Furthermore, the system can be recycled through a number of successive cycles to store and then liberate heat.

A number of different materials can be used to store and liberate heat of crystallization. These materials are hereinafter referred to as "the melt". These materials include sodium sulfate decahydrate, sodium thiosulfate pentahydrate (hypo), sodium chromate decahydrate, calcium chloride hexahydrate, magnesium chloride hexahydrate, magnesium nitrate hexahydrate, urea/ammonium nitrate, disodium hydrogen phosphate dodecahydrate, sodium acetate trihydrate and calcium nitrate trihydrate.

A liquid additive material is included in the supercooled melt. The liquid additive material is preferably a monohydric alcohol or a diol or a triol. When a monohydric alcohol is used, tertiary butyl alcohol or cyclohexanol are preferable. Both of these compounds, due to their molecular structure, have enhanced solubility in salt hydrate melts and low surface tension relative to molten salt hydrates. When a diol is used, ethylene glycol or propylene glycol is preferred. Glycerol is preferred when the liquid additive material is a triol.

When diols or triols are used as the liquid additive material, the liquid additive material provides an optimal effect at a concentration by weight of approximately two percent (2%) to five percent (5%) of the supercooled melt. In this concentration range, and below it, a major fraction of the liquid additive material becomes occluded in the crystals and contributes to the textural control. Below a concentration in the supercooled melt of approximately two percent (2%), the textural effect of the exsolution of liquid additive material in the crystals tends to decrease. As a result, as the concentration of such liquid additive material decreases below approximately two percent (2%), the size of the crystallites produced by exsolution of the liquid-additive material, and the force needed to separate the crystallites becomes larger. Above a concentration of approximately two percent (2%) to five percent (5%) by weight or volume in the supercooled melt, the liquid additive material has only a minor added effect on the exsolution process compared to that provided at a concentration in the range of two percent (2%) to five percent (5%). Furthermore, the heat produced per unit volume of the system decreases because the liquid additive material does not generate any heat when the supercooled melt crystallizes and because the liquid additive material in concentrations above about five percent (5%) causes the solidus temperature of the phase system to drop rapidly. In view of this, except for special purposes, it is desirable to include as little as possible of the liquid additive material in the supercooled melt, consistent with the amount of liquid additive material needed to obtain the desired textural control of the crystalline material formed from the supercooled melt.

As will be appreciated, the supercooled melt tends to crystallize into one single mass or a few large masses in the heat pad if the liquid additive material is not included. The liquid additive material tends to inhibit the formation of such a large mass or such large masses. This results from the formation of adsorbed layers of the additive on the surface of the crystals as they are being formed. This thin film has properties which inhibit the growth of specific faces of the crystals. As a result, the crystals forced to grow by the strong supersaturation in the supercooled melt, overgrow the liquid additive, thereby causing liquid inclusions to form in the crystals. These liquid inclusions coalesce to form laminar vesicles, intersecting segments of the crystals. The formation of the exsolution vesicles causes the crystals to crack and, at slight agitation, to fall apart into smaller crystallites.

The mechanical effect of exsolution on the texture of the crystals formed at nucleation of the supercooled melt is enhanced by gently agitating the heat pads containing the mixture of the supercooled melt and the liquid additive material. This has the effect of accelerating the formation of cracks, releasing the stress on the crystalline material introduced by the exsolution of the liquid additive. Thus, by gently agitating the heat pad as the melt solidifies, the crystalline solid tends to have the texture of sand or silt.

The liquid additive material contributes other important advantages when included in the supercooled melt. For example, when the supercooled melt consists of sodium thiosulfate pentahydrate, the melting temperature and hence the peak temperature of the crystallizing supercooled melt is approximately 118° F. This temperature is higher than that desired for many applications. For example, when the supercooled melt is to be used in heel packs for babies, it preferably should have a melting temperature of approximately 104° F. At this temperature, the heel pack provides an optimal effect in insuring that blood can be drawn effectively from the baby for diagnostic purposes by a heelstick. This temperature is also sufficiently low to prevent overheating of the baby's skin.

The production of an optimal temperature by the nucleation of the supercooled melt is obtained by adding a material such as propylene glycol to the material from which the supercooled melt is produced. For example, when propylene glycol is added by weight in an amount of approximately ten percent (10%) to a supercooled melt such as sodium thiosulfate pentahydrate, the solids temperature decreases to approximately 104° F. from the melting point of the pure salt hydrate at 118° F. Furthermore, the resultant melt is able to exist in a liquid state for extended periods of time at temperatures in the range down to approximately 10° F. This is important in commercial shipments since crystallization of the supercooled melt would otherwise occur at approximatley 40° F. during shipment through cold climates. As will be appreciated, spontaneous crystallization of the supercooled melts in the heat packs during shipment is undesirable since it prevents the heat packs from being used at the destination until the crystallized material has been recycled by melting in the case of heat packs designed for recycling; in the case of heat packs without this provision, the damage is irreversible.

In addition to the materials specified above, other materials then monohydric alcohols and diols and triols may be used as the liquid additive materials, particularly when surface active materials are also included in the system. For example, complex amines may be used. However, such materials tend to be toxic. They also tend to diffuse through the plastic laminates used as containers in current types of heat packs. Certain ketones (such as methyl isobutyl ketone) and esters (such as butyl phthalate, ethyl acetate and oleic acid esters) may also be used.

As previously described, a surface active material may be included in the melt, particularly when the liquid additive material is a monohydric alcohol or some other compound with limited solubility in the melt. The surface active material is provided with properties of solubility both in the salt hydrate melt and in the liquid-additive material and with capability for absorption on one or several crystallographic faces of the salt hydrate crystals. Because of these properties, the surface-absorption material becomes fixed to the different faces of the growing crystals, thereby changing the habit of the crystals and the configuration ratio of the exsolution vesicles forming in the crystals. In this way, the shape and separation of the ultimately forming crystal fragments, and the texture of the aggregate material, can be changed at will within certain limits. As will be seen, the size of the molecules of the surface active material and the structure of their functional groups affect the growth and combination of crystal faces. In effect, the growth of specific crystal faces is being inhibited by the addition of the surface-active materials. As a result, such faces become well developed in the crystals, while fast growing faces become eliminated.

The molecules used as the surface active material may be formed as chains of atoms which may be chosen in different lengths. For example, the surface active molecules may be formed from chains of as many as twelve (12) to twenty-two (22) carbon molecules. When such long chains of atoms are desired, the surface active materials may comprise alkyl sulfates, sulfonates, phosphates or phosphonates.

The surface active material also has the properties of lowering the surface tension between the melt phase and the liquid additive phase so that the latter can be dispersed in the melt and stabilized there as a colloidal suspension which becomes occluded in the growing crystals and eventually exsolves to form texture-controlling vesicles in the crystals. Preferably the surface active materials have hydrophilic properties to accomplish this. When such properties are desired, the surface active materials are preferably alkali salts of acids of the desired molecular types. For example, sodium alkyl sulfate or sulfonates may be used. Such materials are soluble in the salt hydrate melt, and ligate with the water molecules in the melt and on the surface of the salt hydrate crystals.

Alkyl sulfates and phosphates, inorganic phosphates such as polyphosphates, organic phosphates, phosphonates and sulfonates may be used as the surface active material. For example, lecithin (an organic phosphate) and Victawet 12 (a complex organic phosphate manufactured by Victor Chemical Company) may be used.

In addition to being soluble in water, the surface-active material may be soluble in the liquid phase material. For example, lecithin is soluble in pentanol or amyl alcohol isomers (alcohols containing 5 carbon atoms) or cetyl morpholinium ethoxy sulfate made by Imperial Chemical Industries and designated by that company as Atlas G-263.

When both are used, the surface active material and the liquid additive are included in the material such as the supercooled melt in suitable proportions. For example, approximately ten (10) milliliters of the liquid additive material and three (3) milligrams of the surface active material may be mixed in approximately one hundred (100) milliliters of a melt such as the material later providing the supercooled liquid to provide the desired result. However, as little as two (2) to five (5) milliliters of the liquid additive material may be mixed with one half (½) of a milligram of the surface active material in approximately one hundred (100) milliliters of a melt such as the material later providing the supercooled liquid to obtain the desired results. Such a mixture provides a minimal dilution of the material to be melted and crystallized. It also tends to insure that the temperature of the melting and crystallization of the mixture corresponds substantially to the temperature of melting and crystallization of the pure phase or phase system used to produce the supercooled melt. For example, sodium thiosulfate pentahydrate melts at a temperature of approximately 48° C. However, this salt hydrate with small amounts of the surface active material, and with two per cent by weight of propylene glycol as a liquid additive material, starts to melt at a temperature of approximately 47° C. and melts completely at a temperature of approximately 48.5° C.

Various combinations of the above materials provide particularly desirable results. For example, cetyl morpholinium ethoxy sulfate may be used as a liquid additive material in combination with sodium lauryl sulfate as a surface active material or in combination with lecithin as a surface active material; cyclohexanol may be used as a liquid additive material in combination with sodium lauryl sulfate dissolved in propylene glycol, or with Victawet 11, as a surface active material; 2-pentanol may be used as a liquid additive material in combination with lechithin as a surface active material; and tertiary butyl alcohol may be used as a liquid additive material in combination with Victawet 12 as a surface active material.

The combinations disclosed above have certain important advantages. They provide a crystallization of the material such as the supercooled melt as an aggregate forming small lubricated particles which provide an efficient transfer of heat to a patient or other animate or inanimate object receiving the heat. This results in part from the fact that the container holding the crystals is pliant because of the small size and mobility of the crystallites and can accordingly be bent to any desired shape corresponding to the shape of the object to receive the heat. For example, when the mixture 10 is disposed in a container 12 to form a heel pad generally indicated at 14 (FIGS. 4 and 5), the heel pad can be bent into a shape corresponding to the heel of a baby so that the heat released during the crystallization of the material can be applied uniformly over the entire heel area of the baby.

The mixture also has certain other advantages of some importance. For example, the mixture 20 can be disposed in a baby mattress generally indicated at 22 in FIGS. 1, 2 and 3 to warm a baby at a substantially constant temperature for an extended period of time as the baby lies on the mattress. By providing for the crystallization of the supercooled melt systems into an aggregate, forming particles of a small size, the mattress 22 is able to adapt to the contour of the baby so that the baby continues to remain comfortable as heat is liberated from the mattress.

The size, shape and aggregation of the crystallites can be controlled by adjusting the concentration and composition of the liquid additive material in the system. For example, if the liquid additive material forms a relatively concentrated solution in the melt, the crystallites produced are quite small in size. If the liquid additive material is low in concentration, the size of the crystals becomes correspondingly increased. The size of the crystals may be controlled to vary from microscopic size through the size of sand particles to the size of large aggregates. Furthermore, the agitation of the supercooled melt with additives after nucleation facilitates the disruption of the crystalline aggregate, leading to the formation of a large number of small embryonic crystals.

The systems described above can be recycled through a multiple number of uses. For example, the baby mattress 22 described above can be provided with a valve 40. After the supercooled melt in the mixture 20 in the mattress has been produced by heating the mixture to the liquidus temperature of the systems, a nozzle 42 may be inserted into the mattress to nucleate crystallization of the supercooled melt. The nozzle 42 may form a part of the syringe 44 which contains a crystalline powder of sodium thiosulfate pentahydrate. This material has properties of initiating crystallization of the melt into the same form as the nucleating crystals as disclosed and claimed in U.S. Pat. No. 3,951,127 issued to Susan Watson and William Keith Watson and assigned of record to the assignee of record of this application.

The baby mattress 22 is preferably disposed in a cover 46, which offers certain advantages when used with the mattress. The cover 46 may include an outer layer formed from a suitable material such as vinyl and an inner layer formed from a suitable material such as polyurethane so that the cover prevents diffusion of any of the compounds of the system and is pliant. In this way, the sterility of the mattress 22 can be maintained at the same time as the baby lying on the mattress remains comfortable. The cover 46 offers the further advantage that it limits the heat conductivity and thus the temperature applied to the baby if the temperature produced by the melt system is too high for unimpeded application to the skin.

The following constitutes the compositions which have been treated with sodium thiosulfate pentahydrate as the supercooling material:

| Liquid Additive Material | Conc. Vol. % | Surface Active Material | Conc. Vol. % | Weight % |
| --- | --- | --- | --- | --- |
| Ethylene glycol | 1 | — | | |
| " | 2 | — | | |
| " | 3 | — | | |
| " | 4 | — | | |
| " | 5 | — | | |
| " | 10 | — | | |
| " | 2 | Victawet 12 | 0.1 | |
| " | 2 | Victawet 12 | 1.0 | |
| Propylene glycol | 1 | — | | |
| " | 2 | — | | |
| " | 3 | — | | |
| " | 4 | — | | |
| " | 5 | — | | |
| " | 10 | Victawet 12 | 0.1 | |
| " | 2 | Victawet 12 | 1.0 | |
| " | 2 | — | | |
| Glycerol | 1 | — | | |
| " | 2 | — | | |
| " | 4 | — | | |
| " | 10 | — | | |
| " | 2 | Victawet 12 | 0.1 | |
| " | 2 | Victawet 12 | 1.0 | |
| Triethylene glycol | 2 | — | | |
| 1, 5 pentane diol | 2 | — | | |
| n-amyl alcohol | 1.5 | — | | |
| " | 1.5 | Sodium lauryl sulfate | | 0.01 |
| " | 1.5 | Lecithin | | 0.1 |
| " | 1.5 | Sodium propyl sulfonate | | 0.01 |
| t-butyl alcohol | 2 | Victawet 12 | 1.0 | |
| " | 2 | Sodium lauryl sulfate | | 0.01 |
| " | 2 | Lecithin | | 0.1 |
| Cyclohexanol | 1.5 | — | | |
| " | 1.5 | Sodium lauryl sulfate | | 0.01 |
| " | 1.5 | Lecithin | | 0.1 |
| " | 2 | Sodium propyl sulfonate | | 0.01 |
| " | 2 | Victawet 12 | 1.0 | |
| Atlas Chem Co G 263 | 2 | — | | |
| " | 2 | Sodium lauryl sulfate | | 0.01 |
| " | 2 | Victawet 12 | 1.0 | |

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In a method of providing for the formation of crystallites or crystal aggregates of a controlled size and of generating heat at a controlled temperature as a result of the formation of the crystallites or crystal aggregates, providing a melt from sodium thiosulfate pentahydrate with properties of crystallizing in a particular melting temperature interval into a monolithic aggregate, providing a liquid additive material selected from the group consisting of monohydric alcohols, diols and triols and having properties of absorbing on the surface of the crystals and being occluded in the crystals to control the size of the crystallites ultimately produced where the liquid additive material has a weight to approximately ten percent (10%) of the weight of the melt, mixing the melt and the liquid additive material in a percentage of the liquid additive material of approximately ten percent (10%) by weight in the mixture to maintain the temperature of crystallization of the mixture at approximately 104° F. and to inhibit the spontaneous crystallization of the mixture at ambient temperatures approaching the particular melting temperature interval, heating the mixture to a temperature at least equal to the melting temperature interval for a sufficient period of time to convert the melt into a liquid form, and cooling the mixture to a temperature below the melting temperature interval.

2. The method set forth in claim 1 wherein the melt in the mixture is nucleated to form the crystallites of the controlled size and to generate heat as a result of the formation of such crystallites or such crystal aggregates.

3. In a method of providing for the formation of crystallites or crystal aggregates of a controlled size and generating heat, providing sodium thiosulphate pentahydrate having properties of crystallizing into a monolithic mass when nucleated and having properties of providing such crystallization in a melting temperature interval, providing a liquid additive material selected from a group consisting of a monohydric alcohol, diol or triol and having properties of occlusion in the growing crystals and exsolving to separate the growing crystals and limit their size, providing a surface active material selected from a group consisting of sulfates, phosphates, phosphonates and sulfonates and having properties of reducing the surface tension of the liquid additive material on the growing crystals, mixing the melt, the liquid additive material in a weight to approximately ten percent (10%) by weight of the mixture and the surface active material in a weight to approximately five percent (5%) by weight of the mixture, and heating the mixture to a temperature at least equal to the melting temperature interval for a sufficient period of time to convert the mixture to the liquid state, and cooling the mixture to a temperature below the melting temperature interval without nucleating the melt in the mixture.

4. A method as set forth in claim 3 wherein propylene glycol is included in the mixture in a range to approximately ten percent (10%) by weight to control the melting temperature of the mixture and to enhance the ability of the mixture to continue as a liquid at temperatures below the melting temperature interval.

* * * * *